US010045571B2

(12) United States Patent
Thompson

(10) Patent No.: US 10,045,571 B2
(45) Date of Patent: Aug. 14, 2018

(54) BREAST BAND

(76) Inventor: Elizabeth Chabner Thompson, Scarsdale, NY (US)

(*) Notice: Subject to any disclaimer, the term of this patent is extended or adjusted under 35 U.S.C. 154(b) by 1749 days.

(21) Appl. No.: 13/439,021

(22) Filed: Apr. 4, 2012

(65) Prior Publication Data

US 2012/0225606 A1    Sep. 6, 2012

Related U.S. Application Data

(63) Continuation-in-part of application No. 13/411,312, filed on Mar. 2, 2012.

(60) Provisional application No. 61/448,272, filed on Mar. 2, 2011.

(51) Int. Cl.
*A41C 3/00* (2006.01)
*A61F 5/03* (2006.01)
*A61F 13/14* (2006.01)

(52) U.S. Cl.
CPC .............. *A41C 3/0064* (2013.01); *A61F 5/03* (2013.01); *A61F 13/143* (2013.01); *A61F 13/145* (2013.01)

(58) Field of Classification Search
USPC .............. 602/75, 19–20, 60–61; 450/79–80, 450/82–85, 1, 39; 2/463–465; 482/13; 128/874–876
See application file for complete search history.

(56) References Cited

U.S. PATENT DOCUMENTS

| | | | | |
|---|---|---|---|---|
| 2,338,535 A * | 1/1944 | Pfleumer | ........................ | 441/113 |
| 2,412,075 A * | 12/1946 | Boone | .............................. | 602/19 |
| 2,749,552 A * | 6/1956 | Feste | .......................... | A61F 5/03 2/92 |
| 2,800,902 A * | 7/1957 | Wiltrout | ................ | A61F 13/143 450/1 |
| 3,077,196 A * | 2/1963 | Paxton | ........................... | 450/39 |
| 3,945,041 A * | 3/1976 | Rhee | .................................. | 2/463 |
| 4,508,110 A * | 4/1985 | Modglin | ......................... | 602/19 |
| D353,202 S * | 12/1994 | Hong | ............................ | D24/190 |
| 6,155,996 A * | 12/2000 | Van Brunt et al. | ............. | 601/41 |
| 6,336,839 B1 * | 1/2002 | Valli | ................................. | 450/1 |
| 8,550,871 B1 * | 10/2013 | Baratta | .......................... | 450/39 |
| 8,790,154 B2 * | 7/2014 | Blackwell | ....................... | 450/86 |
| 2006/0211334 A1 * | 9/2006 | Smith | ................................ | 450/1 |
| 2006/0228989 A1 * | 10/2006 | Chou et al. | ..................... | 450/81 |

* cited by examiner

*Primary Examiner* — Alissa Thompkins
*Assistant Examiner* — Brieanna Szafran
(74) *Attorney, Agent, or Firm* — Kaplan Breyer Schwarz, LLP

(57) ABSTRACT

In some embodiments, a breast band includes a non-resilient, inelastic band and an adjustable closure for suitably tightening the band around the upper chest of a wearer in order to prevent the breasts from rising to an unnaturally high position. In some embodiments, the breast band also includes two axilla-accommodating regions or two nascent axilla-accommodating regions.

16 Claims, 6 Drawing Sheets

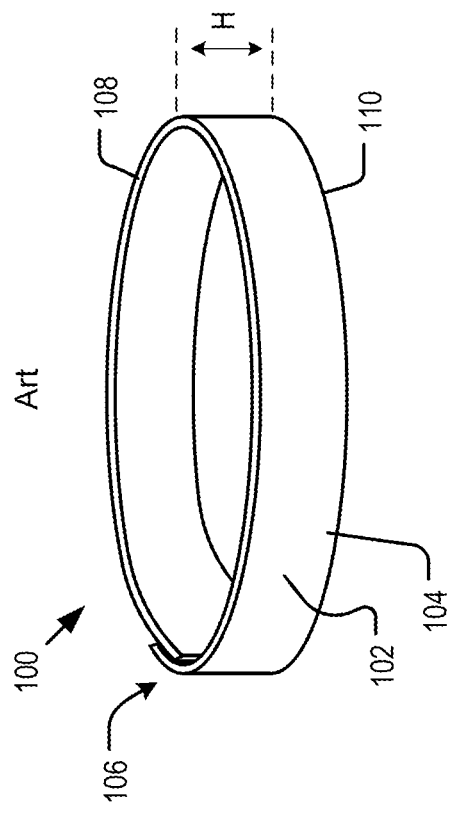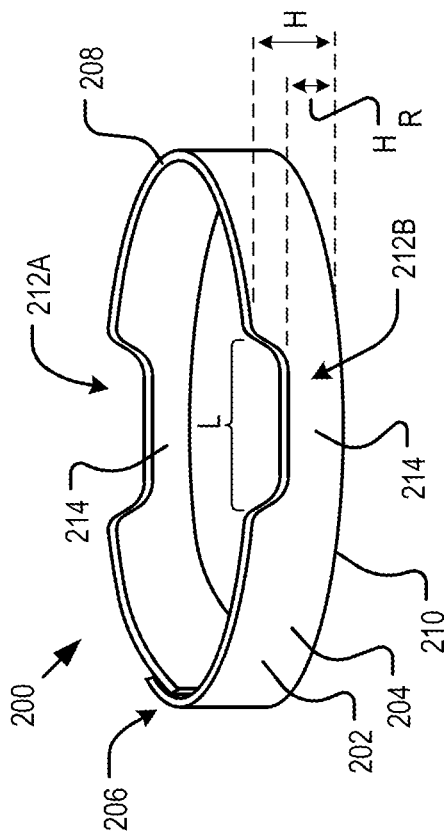

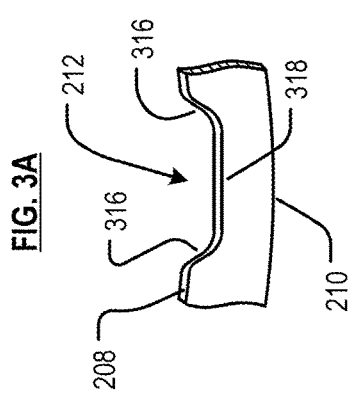
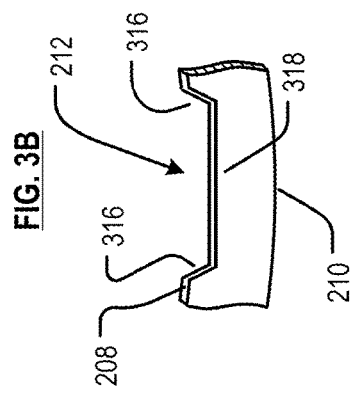
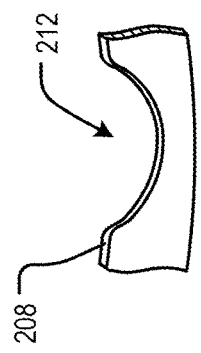

BREAST BAND

STATEMENT OF RELATED CASES

This case is a continuation-in-part of U.S. patent application Ser. No. 13/411,312 filed Mar. 2, 2012, which is incorporated by reference herein and which claims priority of Provisional Patent Application Ser. No. 61/448,272 filed Mar. 2, 2011.

FIELD OF THE INVENTION

The present invention relates to an article for use after breast augmentation surgery and breast reconstruction surgery in which expanders and/or implants are used.

BACKGROUND OF THE INVENTION

After breast augmentation or reconstruction (using expanders and implants), it usually necessary to exert, for a period of a few weeks, downward pressure on the breast implant to stabilize it, keep the implant in its correct position, and prevent it from rising to settle in an unnaturally high position. To accomplish this, physicians will typically recommend that the patient wear a breast band or binder that ensures that the implants settle in the infra-mammary crease in a natural position.

FIG. 1 depicts breast band 100, which is typical of a breast band in the prior art. This known breast band includes band 102, overwrap 104, and adjustable closure 106. Band 102 is usually formed from a resilient, elastic material. The band is typically a few inches in height. The height H of band 100, which is measured between upper edge 108 and lower edge 110 of the band 102, is constant. It is to be understood that the terms "upper" and "lower," when used to reference a particular "edge" of the band, refer to the respective locations of the edges when the band is being worn by a patient.

Manufacturers of breast bands understand that the bands will be worn for relatively long periods of time (weeks). As a consequence, the bands often include overwrap 104, which is a soft, moisture-absorbent material that overlies band 102 and is intended to contact the skin of a wearer. The overwrap offers a measure of comfort to the wearer. Adjustable closure 106 enables the band to opened, as is required to place the band around the wearer's upper chest (or remove it), and to be closed so that the band remains on the wearer. The adjustable nature of the closure accommodates different body sizes, etc.

Notwithstanding manufacturers' efforts, patients routinely complain that the bands are uncomfortable. Typical complaints are that the band is too tight, tends to crease or fold over, irritates the skin and surgical incisions, and cuts into the axilla (armpit).

SUMMARY OF THE INVENTION

The present invention provides a breast band that avoids some of the shortcomings of the prior art. In particular, by virtue of its construction, the breast band will not crease or fold over nor will it cut into the axilla.

In the illustrative embodiment, the breast band comprises an elastic material, covered with a soft, moisture-absorbent material and having a hook-and-loop type (Velcro®) closure. Furthermore, breast bands in accordance with the present teachings are configured to provide two axilla-accommodating regions.

The axilla-accommodating regions provide a reduced height relative to the rest of the breast band. In some embodiments, the breast band, as manufactured, provides two, reduced-height, axilla-accommodating regions. In particular, the upper edge of the breast band (when in use) in the axilla-accommodating regions is "lower" than the upper edge of the rest of the breast band, as if a portion of the band were "cut-out" or removed. As such, the height of the band is less in the axilla-accommodating regions than the rest of the band. The axilla-accommodating regions are located on opposed portions of the breast band (when the two ends of the band are brought together).

In some other embodiments, rather than being manufactured with reduced-height axilla-accommodating regions, the breast band is physically adapted to enable a purchaser/therapist/wearer to remove portions of the breast band to create the axilla-accommodating regions.

In some additional embodiments, the breast band comprises a non-resilient, non-elastic, etc., material, with or without axilla-accommodating regions. The inventor recognized that if the breast band includes an adjustable closure, then the band itself need not be resilient/elastic. Rather, the adjustable closure provides the requisite tightness; that is, it is able to cinch the breast band suitably tight to prevent the breasts from rising to an unnaturally high position. Patient-to-patient variation in girth of the upper chest is accommodated by the length of the band and to a minor extent, depending upon its design, by the adjustable closure. The inventor recognized that this approach increases the variety of materials that can be used to form the breast band.

For example, in some embodiments, the breast band is formed from a material that is characteristically thinner than the resilient materials typically used for breast bands. Or, the material can be chosen to provide some other desirable property or characteristic. For example, in some embodiments, the breast band is formed from a transparent material, such as Clear-Fit TPU brand thermoplastic polyurethane, commercially available from Fulflex, Inc. of Brattleboro, Vt. The use of thinner material and/or transparent material results in a breast band that is likely to be less noticeable under a wearer's clothing. Other benefits can accrue from using other materials—materials that would otherwise not be suitable for use with the breast band since they are not resilient/elastic.

When the band is worn, embodiments that include the axilla-accommodating regions are positioned such that the axilla-accommodating regions are beneath each axilla. This accommodates motion of the upper arms and prevents the irritation that tends to otherwise occur. In addition, the relatively lower upper edge of the band in the axilla-accommodating regions substantially reduces the likelihood that the breast band will crease or fold over in use, as would otherwise occur due to the movement of the upper arm. Such creasing and folding is uncomfortable for the wearer, results in unflattering lines/bulges under the user's outerwear, and can be a further source of irritation.

BRIEF DESCRIPTION OF THE DRAWINGS

FIG. 1 depicts breast band 100 in the prior art.

FIG. 2 depicts breast band 200 in accordance with the illustrative embodiment of the present invention.

FIGS. 3A-3C depict a partial view of breast band 200 depicting various contours for an axilla-accommodating region.

DETAILED DESCRIPTION

Figure 4A:
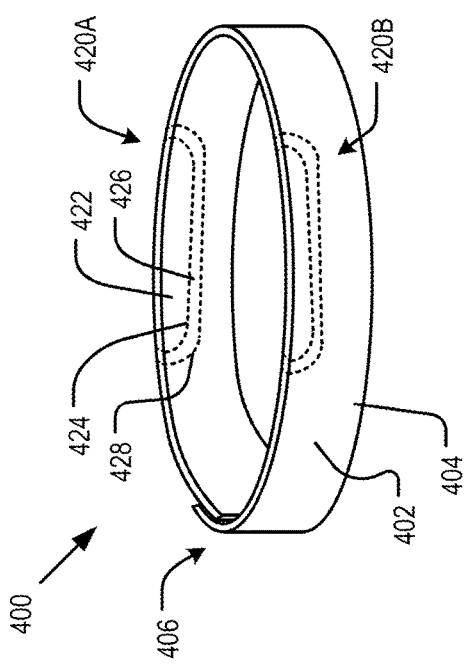
FIG. 4A depicts breast band 400 in accordance with an embodiment of the present invention including nascent axilla-accommodating regions.

FIG. 2 depicts breast band 200 in accordance with the illustrative embodiment of the present invention. Breast band 200 comprises band 202, optional overwrap 204, adjustable closure 206, and axilla-accommodating regions 212A and 212B (collectively referenced "212").

Band 202 is typically formed from a resilient, elastic material, such as Gore elastic. The height, H, of band 202, as measured between upper edge 208 and lower edge 210 is typically in a range of about 5 to 7.5 centimeters (2 to 3 inches), other than at axilla-accommodating regions 212. Optional overwrap 204 is a soft, moisture-absorbent material that overlies band 202 and is intended to contact the skin of a wearer. The overwrap 204 is usually a material such as chamois cotton cloth or looped fabric (e.g., terrycloth, etc.). In some embodiments, band 202 is formed from a material that has a suitably soft exterior surface such that overwrap 204 is omitted.

Breast band 200 must be "suitably tight" when worn. As used in this Description and the attached Claims, the term "suitably tight" or "suitably tightly" when used in the context of the fit of the breast band to a wearer, means that the band is tight enough (or is capable of being adjusted tight enough) to accomplish its intended purpose, which is to prevent the breasts from rising to an unnaturally high position. Due to the wide range of variability in the girth of the upper chest from patient to patient, band 202 is available in several lengths to provide the requisite fit (e.g., a first length that accommodates individuals having an upper chest girth of 30-35 inches, a second length that accommodates individuals having an upper chest girth of 35-40, a third length for an upper chest girth of 40-45, and a fourth length for an upper chest girth of 45-50, etc). Medical practitioners skilled in the art will be able to determine when the fit of the breast band is "suitably tight" and will also be able to determine in how many lengths to make the band available to ensure that for all wearers.

Adjustable closure 206 enables the band to opened, as is required to place the band around the wearer's upper chest (or remove it therefrom), and to be closed so that the band remains on the wearer. The adjustable nature of the closure also accommodates some adjustability as to the relative tightness of the band about the wearer's upper chest. In some embodiments, the adjustable closure comprises two strips of hook-and-loop fastener (i.e., Velcro®), one disposed on each end of band 202. Other adjustable closure mechanisms can suitably be used as long as they are not a source of discomfort to the wearer.

Axilla-accommodating regions 212 comprise reduced-height portions 214 of band 202. The orientation of breast band 200, as depicted in FIG. 2, is the orientation in which the band is fitted to a wearer; that is, edge 208 is superior (higher) and edge 210 is inferior (lower). Thus, in the axilla-accommodating regions, upper edge 208 "dips" such that height $H_R$ between the upper edge of band 202 in the axilla-accommodating region and lower edge 210 of band 202 is reduced relative to the height H of the balance of band 202. Upper edge 208 of band 202 in axilla-accommodating regions 212 is at least about 1.25 centimeters (0.5 inches) "lower" than the upper edge of band 202 at other locations, and more preferably at least 2.5 centimeters (1 inch) "lower."

Length L of axilla-accommodating regions 212 is sufficient to span the axilla regions of a wearer. Typically, the length L of the axilla-accommodating regions will be at least about 10 centimeters (4 inches), but can be less, and typically in a range of about 10 to 15 centimeters (4 to 6 inches).

Axilla-accommodating regions 212 can have any of a number of "profiles," a few of which are depicted in FIGS. 3A to 3C. As depicted in FIG. 3A, in some embodiments, upper edge 208 of the band in axilla-accommodating regions 212 is contoured such that, in profile, it drops along a smooth curve in regions 316 near each end of region 212 and flattens in region 318 such that it is parallel to lower edge 210.

FIG. 3B depicts an embodiment wherein upper edge 208 of the band in axilla-accommodating regions 212 is contoured such that, in profile, it drops at an angle, but linearly, in regions 316 near each end of region 212 and flattens in region 318 such that it is parallel to lower edge 210.

FIG. 3C depicts an embodiment wherein upper edge 208 of the band in axilla-accommodating regions 212 has a substantially arcuate profile. Other profiles for axilla-accommodating regions 212, as will occur to those skilled in the art in light of the present disclosure, may suitably be employed.

FIG. 4A depicts breast band 400 in accordance with an embodiment of the present invention. Like breast band 200, breast band 400 includes band 402, optional overwrap 404, and adjustable closure 406.

Unlike breast band 200, which includes "preformed" axilla-accommodating regions 212, breast band 400 includes nascent axilla-accommodating regions 420A and 420B (collectively referenced "420"). That is, breast band 400 is configured so that portions of the band can be removed to form axilla-accommodating regions. But the axilla-accommodating regions do not exist until portions of band 402 are removed by a purchaser, patient, therapist, etc.

In the embodiment shown, each nascent axilla-accommodating region 420 comprises "fissures" 424 and 428. In preferred embodiments, fissures 424 and 428 are regions at which a portion of band 402 is readily separated from the remainder of the band. For example, fissure 424 can be rouletting, perforations, or the like that enable portion 422 of band 402 to be removed. Likewise, fissure 428 can be rouletting, perforations, etc., that enable band portions 426 and 422 of band 402 to be removed. In some less preferred embodiments, rather than including a fissure, a "cut" line can be indicated, wherein a pair of scissors, etc., is used to cut the band to create the axilla-accommodating regions.

Although breast band 400 includes two fissures 424 and 428, in some other embodiments, breast band 400 includes only a single fissure. In some further embodiments, breast band 400 includes more than two fissures. The greater the number of fissures in back band 400, the greater the ability to tailor the axilla-accommodating regions to meet the individual needs of a given patient.

In embodiments in which breast band 400 comprises multiple layers of material, such as when overwrap 404 is present, it is important that when the portions of band 402 are removed to form the axilla-accommodating regions, the multiple layers remain joined. That is, for example, overwrap 404 must not separate from the material comprising band 402 at fissure 424 when band portion 422 is removed.

Figure 4B:
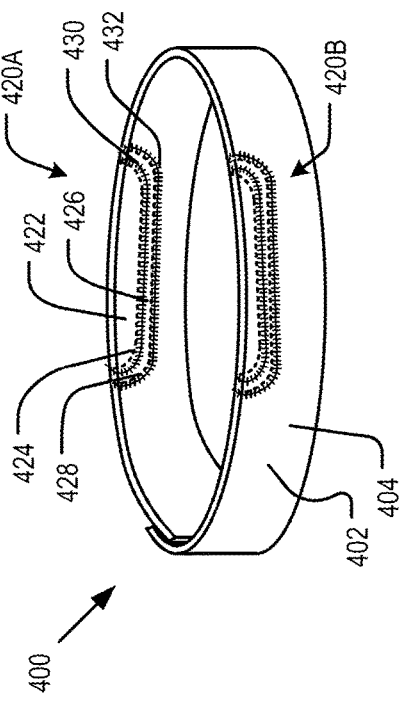
FIG. 4B depicts breast band 400 in accordance with an embodiment of the present invention including nascent axilla-accommodating regions and seams.

As a consequence, in some such embodiments, band 402 further comprises "seams" 430 and 432, such as depicted in the embodiment of breast band 400 that is depicted in FIG. 4B. The seams are a line-of-junction where the layers are joined. The seams can be formed by an ultrasonic weld, any of a variety of heat-joining techniques, stitches, or via any other technique known in the art.

As depicted in FIG. 4B, seam 430 is "below" fissure 424 and seam 432 is below fissure 428. Thus, when band portion 422 is removed at fissure 424, nearby-seam 430 ensures that overwrap 404 does not separate from band 402. Likewise, seam 432 enables band portions 422 and 426 to be removed without the aforementioned separation.

Fissures 424 and 428 and seams 430 and 432 are depicted and described as distinct features. It is to be understood, however, that in other embodiments, the functionality of the fissures and the functionality of the seams can be integrated into a single feature that is capable of functioning as a line of separation but that is also capable of keeping multiple layers of material (e.g., band 402 and overwrap 404, etc.) joined together. The separation of these functions into distinct features is primarily for pedagogical purposes.

Figure 5:
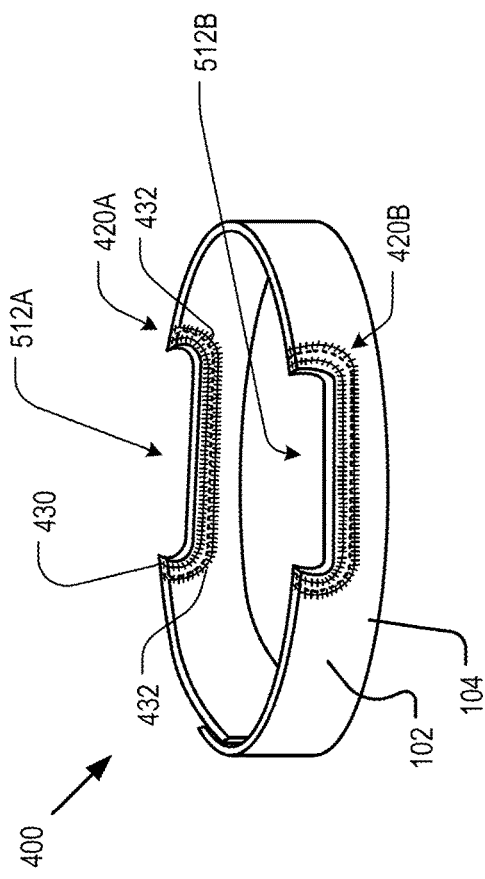
FIG. 5 depicts breast band 400 of FIG. 4B, wherein the axilla-accommodating regions are formed by removing first portions of the breast band.

FIG. 5 depicts breast band 400 with band portion 422 removed, thereby forming axilla-accommodating regions 512A and 512B. Note that although band portion 422 is removed at fissure 426, seam 430 remains to ensure that band 402 and overwrap 404 do not separate. Also, band portion 426, fissure 428, and seam 432 are intact.

Figure 6:
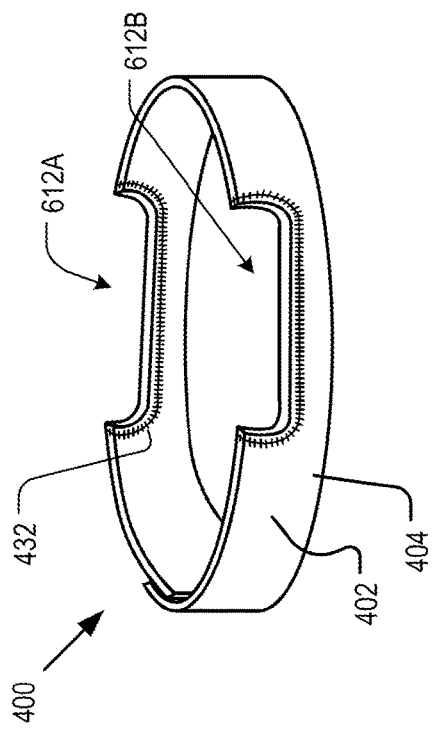
FIG. 6 depicts breast band 400 of FIG. 4B, wherein the axilla-accommodating regions are formed by removing second portions of the breast band.

FIG. 6 depicts breast band 400 with both of band portions 422 and 426 removed, thereby forming axilla-accommodating regions 612A and 612B than are "deeper" than axilla-accommodating regions 512A and 512B, wherein only portion 422 was removed.

Figure 7:
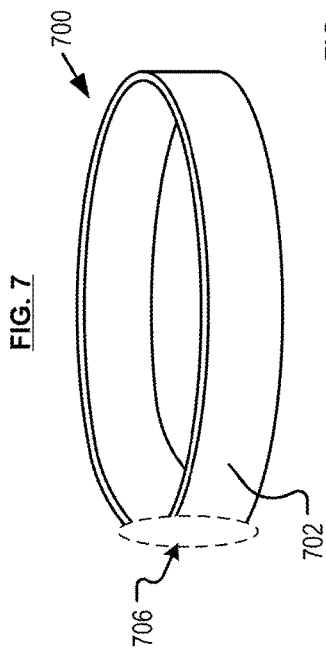
FIG. 7 depicts breast band 700 in accordance with an embodiment of the present invention including a non-resilient band and an adjustable closure.

FIG. 7 depicts breast band 700 in accordance with a further embodiment of the present invention. Breast band 700 includes band 702 that is formed from a non-resilient, non-elastic material. One such non-resilient, non-elastic material that is contemplated for use is a transparent material, such as Clear-Fit TPU brand thermoplastic polyurethane. When a very thin material is used to form band 702, the upper and lower edges of the band may need to be reinforced to prevent the band from curling/folding over. This can be accomplished, for example, by folding the upper and lower edges over to create a thin "hem," etc.

In embodiments in which the band is formed from a non-resilient/inelastic material, as opposed to being formed from resilient material, it must be sized to a greater degree of specificity for a given patient. For example, patient-to-patient variation in the girth of the upper chest can vary by twenty inches or more. Most female patients, for example, will fall in a range of between about 30 inches to about 50 inches for the girth of the upper chest. As a consequence, the length of the band will typically fall within the aforementioned range and is sized for a specific patient.

Although band 702 is typically used without an overwrap (e.g., for comfort, etc.), an overwrap can be used in conjunction with band 702.

Breast band 700 also includes adjustable closure 706. In view of non-resilient band 702, the adjustable closure permits the band to be suitably tightened about the upper chest, thereby enabling the breast band to provide its intended function (i.e., preventing the breasts from rising to an unnaturally high position). Furthermore, adjustable closure 706 provides for some variation in the length of the band. For example, an adjustable closure implemented as strips of hook-and-loop fastener (i.e., Velcro®) at each end of the band that are intended to overlap (such as shown in FIG. 2) will typically provide a few inches of adjustability. As such, a band having a given length can be suitable for a small range (a few inches) of variation in the girth of the upper chest of the wearer, as a function of the length of the strips of hook-and-loop fastener. For example, in various embodiments, breast band 700 is suitable for the following variation in girth of the upper chest:

Embodiment 1: 2 inch variation;
Embodiment 2: 3 inch variation;
Embodiment 3: 4 inch variation.

These embodiments are provided by way of illustration, not limitation.

Other adjustable closure mechanisms can suitably be used as long as they are not a source of discomfort to the wearer. Such other mechanisms will have an associated range of adjustability.

Figure 8:
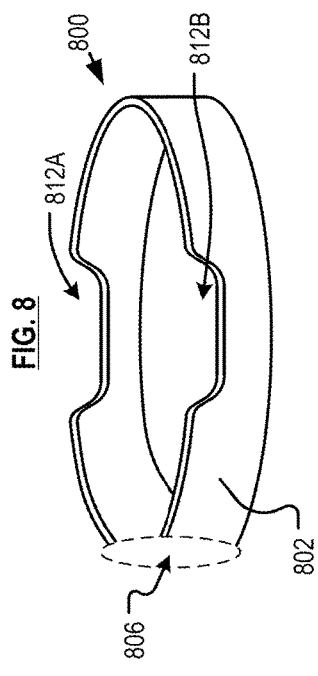
FIG. 8 depicts breast band 800 in accordance with an embodiment of the present invention including a non-resilient band, adjustable closure, and axilla-accommodating regions.

FIG. 8 depicts breast band 800 in accordance with a further embodiment of the present invention. Breast band 800 includes band 802 that is formed from a non-resilient, non-elastic material, such as the aforementioned Clear-Fit TPU brand thermoplastic polyurethane. Although band 802 is typically used without an overwrap (e.g., for comfort, etc.), an overwrap can be used in conjunction with band 802. Breast band 800 also includes adjustable closure 806.

Breast band 800 further includes axilla-accommodating regions 812A and 812B (collectively referenced "812"). Axilla-accommodating regions 812 are the same as axilla-accommodating regions 212 previously discussed in conjunction with FIGS. 2 and 3A-3C.

Figure 9:
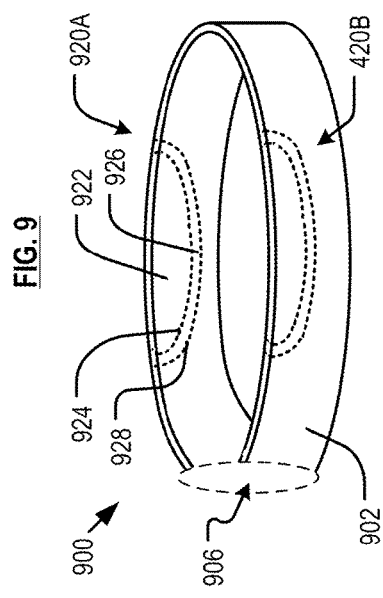
FIG. 9 depicts breast band 900 in accordance with an embodiment of the present invention including a non-resilient band, adjustable closure, and nascent axilla-accommodating regions.

FIG. 9 depicts breast band 900 in accordance with a further embodiment of the present invention. Breast band 900 includes band 902 that is formed from a non-resilient, non-elastic material, such as the aforementioned Clear-Fit TPU brand thermoplastic polyurethane. Although band 902 is typically used without an overwrap (e.g., for comfort, etc.), an overwrap can be used. Breast band 900 also includes adjustable closure 906.

Breast band 900 includes nascent axilla-accommodating regions 920A and 920B (collectively referenced "920"). These nascent regions 920 are the same as regions 420 discussed in conjunction with FIG. 4A. Specifically, each nascent axilla-accommodating region 920 comprises "fissures" 924 and 928. In preferred embodiments, fissures 924 and 928 are regions at which a portion of band 902 is readily separated from the remainder of the band. For example, fissure 924 can be rouletting, perforations, or the like that enable portion 922 of band 902 to be removed. Likewise, fissure 928 can be rouletting, perforations, etc., that enable band portions 926 and 922 of band 902 to be removed. In some less preferred embodiments, rather than including a fissure, a "cut" line can be indicated, wherein a pair of scissors, etc., is used to cut the band to create the axilla-accommodating regions.

Although breast band 900 includes two fissures 924 and 928, in some other embodiments, breast band 900 includes only a single fissure. In some further embodiments, breast band 900 includes more than two fissures. The greater the number of fissures in back band 900, the greater the ability to tailor the axilla-accommodating regions to meet the individual needs of a given patient.

Figure 10:
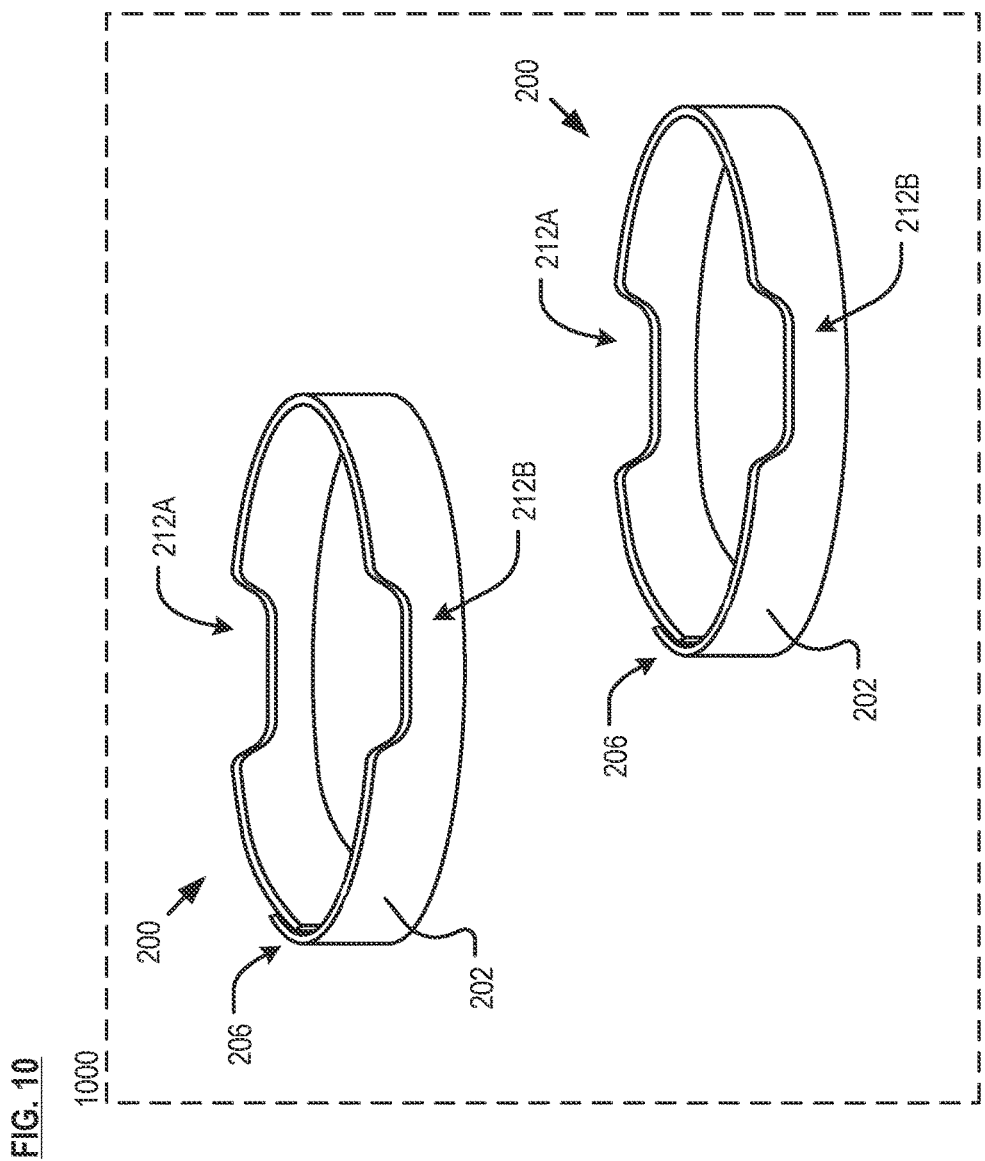
FIG. 10 depicts a kit in accordance with an embodiment of the present invention, wherein the kit includes two breast bands of the present teachings.

FIG. 10 depicts kit 1000 having two breast bands in accordance with the present teachings. FIG. 10 depicts two of breast bands 200, as depicted in FIG. 2. As previously disclosed, each breast band 200 includes band 202, adjustable closures 206, and two axilla-accommodating regions 212A and 212B. In other embodiments, the kit can include any of the breast bands disclosed herein. In some embodiments, the two breast bands have a different size from one another. For example, one of the bands has a length suitable for encircling an upper chest of a wearer in a first group having an upper chest with a girth in a first range and the other of the bands have a length that is suitable for encircling an upper chest of a wearer in a second group having an upper chest with a girth in a second range, wherein at least some of the girths in the two ranges are different.

It is to be understood that many variations of the invention can easily be devised by those skilled in the art after reading this disclosure and that the scope of the present invention is to be determined by the following claims.

What is claimed is:

1. A breast band for preventing a breast implant from settling in an unnaturally high position, comprising:
    a band, wherein the band is a non-resilient, inelastic material, and wherein the band is long enough to encircle an upper chest of a wearer; and
    an adjustable closure, wherein the adjustable closure:
        (a) opens and closes the band; and
        (b) enables the band to be adjusted suitably tightly about the upper chest of the wearer to apply downward pressure on the breast implant.

2. The breast band of claim 1 further comprising one of:
    (i) first and second axilla-accommodating regions, wherein the first and second axilla-accommodating regions have a reduced height such that in the first and second axilla-accommodating regions, the upper edge of the breast band is lower than the upper edge of the rest of the band; or
    (ii) first and second pre-defined nascent axilla-accommodating regions, wherein each nascent axilla-accommodating region comprises a first physical adaptation that facilitates removal of a pre-defined portion of the band, thereby forming an axilla-accommodating region having a reduced height such that in the first and second axilla-accommodating regions, the upper edge of the breast band is lower than the upper edge of the rest of the band.

3. The breast band of claim 2 wherein the first physical adaptation is a fissure in each nascent axilla-accommodating region, wherein the fissure facilitates removal of the portion of the band to provide the axilla-accommodating region.

4. The breast band of claim 2 wherein the first physical adaptation comprises a cut line, wherein, a user cuts the band along the cut line to remove the portion of the band, thereby forming the axilla-accommodating region.

5. The breast band of claim 2 wherein the band has a height in a range of about 2 to 3 inches, as measured between an upper edge and a lower edge of the band.

6. The breast band of claim 1 wherein the breast band comprises a transparent material.

7. The breast band of claim 1 wherein the breast band comprises thermoplastic polyurethane.

8. A kit comprising:
    a first breast band including:
        a first band, wherein the first band comprises a non-resilient, inelastic material, and wherein the first band has a length suitable for encircling an upper chest of a wearer in a first group having an upper chest with a girth in a first range;
        an adjustable closure, wherein the closure enables the first band to be opened and closed and to be adjusted suitably tightly about an upper chest of a wearer in the first group; and
    a second breast band including:
        a second band, wherein the second band comprises a non-resilient, inelastic material, and wherein the second band has a length suitable for encircling an upper chest of a wearer in a second group having an upper chest with a girth in a second range;
        an adjustable closure, wherein the closure enables the second band to be opened and closed and to be adjusted suitably tightly about an upper chest of a wearer in the second group; and
    wherein a girth in the first range is smaller than a girth in the second range.

9. The kit of claim 8 and further wherein:
    the first breast band comprises first and second axilla-accommodating regions, wherein the first and second axilla-accommodating regions of the first breast band have a reduced height such that in the first and second axilla-accommodating regions, an upper edge of the first breast band is lower than an upper edge of the rest of the first band; and
    the second breast band comprises first and second axilla-accommodating regions, wherein the first and second axilla-accommodating regions of the second breast band have a reduced height such that in the first and second axilla-accommodating regions, an upper edge of the second breast band is lower than an upper edge of the rest of the second band.

10. The kit of claim 9 wherein at least one of the first and second breast bands comprises transparent material.

11. The kit of claim 9 wherein at least one of the first and second breast bands comprises thermoplastic polyurethane.

12. The kit of claim 9 wherein at least one of the first and second breast band has a height in a range of about 2 to 3 inches, as measured between an upper edge and a lower edge of thereof.

13. The kit of claim 8 and further wherein:
    the first breast band comprises first and second pre-defined nascent axilla-accommodating regions, wherein each nascent axilla-accommodating region of the first breast band comprises a first physical adaptation that facilitates removal of a pre-defined portion of the first band, thereby forming an axilla-accommodating region having a reduced height relative to the rest of the first band; and
    the second breast band comprises first and second pre-defined nascent axilla-accommodating regions, wherein each nascent axilla-accommodating region of the second breast band comprises a first physical adaptation that facilitates removal of a pre-defined portion of the second band, thereby forming an axilla-accommodating region having a reduced height relative to the rest of the second band.

14. The kit of claim 13 wherein the first physical adaptation comprises one of either:
   (a) a fissure, wherein the fissure facilitates removal of the pre-defined portion of the first band and the second band to provide the axilla-accommodating regions; and
   (b) a cut line, wherein, a user cuts the first band and the second band along the cut line to remove the pre-defined portion of the respective first band and second band, thereby forming the axilla-accommodating regions.

15. The kit of claim 8 wherein the first range is two inches and wherein girths in the second range will be at least 2 inches greater than the smallest girth of the first range.

16. The kit of claim 8 wherein the first range is three inches and wherein girths in the second range will be at least 3 inches greater than the smallest girth of the first range.

* * * * *